United States Patent [19]

Radosevich et al.

[11] Patent Number: 4,756,346
[45] Date of Patent: Jul. 12, 1988

[54] PROCESS AND APPARATUS FOR THE PREPARATION OF MULTIPLE GRADIENTS

[75] Inventors: James A. Radosevich, Chicago, Ill.; Steven Barclay, Madison, Wis.

[73] Assignee: The United States of America as represented by the Department of Health and Human Services, Washington, D.C.

[21] Appl. No.: 903,879

[22] Filed: Sep. 2, 1986

[51] Int. Cl.$^4$ .............................................. B65B 3/04
[52] U.S. Cl. ......................................... 141/9; 141/67; 141/234; 422/179; 422/180
[58] Field of Search ..................... 422/100, 63, 81, 82, 422/179, 180; 141/99–110, 234–245, 37–66, 67, 1–12

[56] References Cited

U.S. PATENT DOCUMENTS 4,459,864 7/1984 Rincione ........................... 422/100

Primary Examiner—Houston S. Bell, Jr.
Attorney, Agent, or Firm—Browdy and Neimark

[57] ABSTRACT

Method and apparatus are provided for making multiple continuous or discontinuous gradients. Individual vacuum systems draw the gradient material from a common mixing chamber and deliver it into identical receptacles where each gradient is formed. A battery of syringes can be used to create vacuums on each individual chamber, and an opposing battery of syringes can be used to deliver gradient material to the mixing chamber. By varying the ratio of syringes generating vacuums to syringes delivering gradient material and/or initial solution volumes, gradients of various shapes can be produced.

7 Claims, 3 Drawing Sheets

4,756,346

PROCESS AND APPARATUS FOR THE PREPARATION OF MULTIPLE GRADIENTS

FIELD OF THE INVENTION

The present invention relates to a gradient former which can produce continuous and/or step gradients.

BACKGROUND OF THE INVENTION

Continuous and discontinuous gradients are used to separate a wide variety of components including cells and subcellular components. Several gradient makers are commercially available. These gradient formers lack the versatility to deliver both multiple identical continuous and discontinuous gradients. None of the gradient makers presently available is able to make multiple gradients of analytical quality. These gradient makers are often difficult to regulate and require time consuming manipulations.

Gradients are usually generated by devices which have two chambers. One of the chambers serves as the mixing chamber, and from this reservoir one or more delivery lines and a pump are used to transfer the gradients to their receivers. This method permits one to form several gradients, but, unfortunately, the gradients are often of unequal volume and/or unequal gradient shape. These defects occur when the flow rates of the gradient material in the delivery lines are unequal due to small differences in the diameters of the tubing.

A number of devices have been disclosed for providing samples of different dilutions, although most of these devices are rather complex. Buckley, in U.S. Pat. No. 3,525,592, discloses a liquid sampling device for continuously taking measured samples of blood and diluting them with measured quantities of liquid. The apparatus comprises a probe, a first syringe, the cylinder of which is connected to the probe by a closed conduit, a second syringe, the cylinder of which is connected by a second closed conduit to a liquid diluent container, a third closed conduit connecting the second conduit to the first conduit, a two-way valve between the second and third conduits, and means for actuating the syringes and valves so that the first syringe draws a measured volume of sample into the probe and ejects it therefrom, and the second syringe ejects a measured volume of diluent from the container through the probe behind the ejected sample.

Feichtmeir et al., in U.S. Pat. No. 3,127,062, discloses a semiautomatic sampling and diluting apparatus comprising a first powered precision displacement volumetric chamber for measuring and delivering a fluid from the chamber, and a second similar chamber for measuring and delivering a second fluid in admixture with the first. A precision ground plunger is provided in the volumetric chambers. Feichtmeier, in U.S. Pat. No. 3,102,863, discloses a calibrated pipette which forms a means into which a predetermined volume of fluid sample may be drawn, and a variable volume chamber means which may be calibrated to contain a predetermined volume of diluent or reagent. Control valve means are provided which in a first position simultaneously connect the chamber with a storage reservoir source so that the predetermined volume of diluent may be introduced into the chamber and the desired volume of sample may be drawn into the pipette.

Sequeira, in U.S. Pat. No. 3,327,535, discloses a multiple pipette apparatus including a line of pipetting tubes mounted on a member extending along a support, the tubes individually communicating through pipes with piston-and-cylinder units operated in synchronism to draw liquid simultaneously from the pipetting tubes.

These prior devices do not provide serial dilutions of continuous and discontinuous gradients, and using varying ratios of batteries of syringes generating vacuum to syringes delivering gradient material.

SUMMARY OF THE INVENTION

It is, accordingly, an object of the invention to overcome deficiencies in the prior art, such as indicated above.

It is another object to provide a process and apparatus for forming multiple identical serial dilutions of continuous and/or discontinuous materials, or combinations thereof.

It is a further object of the present invention to provide a process and apparatus that can produce either multiple identical continuous and/or discontinuous gradients or variations thereof.

It is yet a further object of the present invention to provide a process and apparatus that can produce continuous and/or discontinuous gradients of varying degrees and/or combinations thereof.

It is a still further object of the present invention to produce step gradients which will have well-defined interfaces.

The present invention provides a process and apparatus that can be used to produce multiple continuous and/or discontinuous gradients. Continuous gradients of shapes ranging from linear to concave or convex, and step gradients with well-defined interfaces, can be provided. Identical gradients are generated by using identically metered vacuums. Each individual vacuum system draws the gradient material from a common mixing chamber and delivers it into identical receptacles where each gradient is formed. This process is achieved by using a battery of syringes or other devices to create vacuums on each individual chamber and an opposing battery of syringes or other devices to deliver gradient material to the mixing chamber. By varying the ratio of means for generating vacuums to means for delivering gradient material and/or initial solution volumes, or by varying the ratio of the size of the devices generating vacuums to devices delivering gradient material, gradients of various shapes can be produced.

For example, a vacuum pump with an appropriate valve system can be used instead of syringes. Other devices which operate in the same manner can readily be substituted for the syringes.

For a better understanding of the invention, as well as the above and other objects and the nature and advantages thereof, a possible embodiment thereof will now be described with reference to the attached drawing, which is offered illustratively.

DETAILED DESCRIPTION OF THE INVENTION

The apparatus of the present invention can be used to produce multiple continuous and/or discontinuous gradients. Gradient material is kept in a mixing chamber 10, and is delivered through delivery lines 11 to receptacles to form a gradient. Individual vacuum systems 13 draw material from the mixing chamber and individual means 14 are provided each receptacle for receiving liquid through the delivery lines 11 into each receptacle 12.

Figure 2:
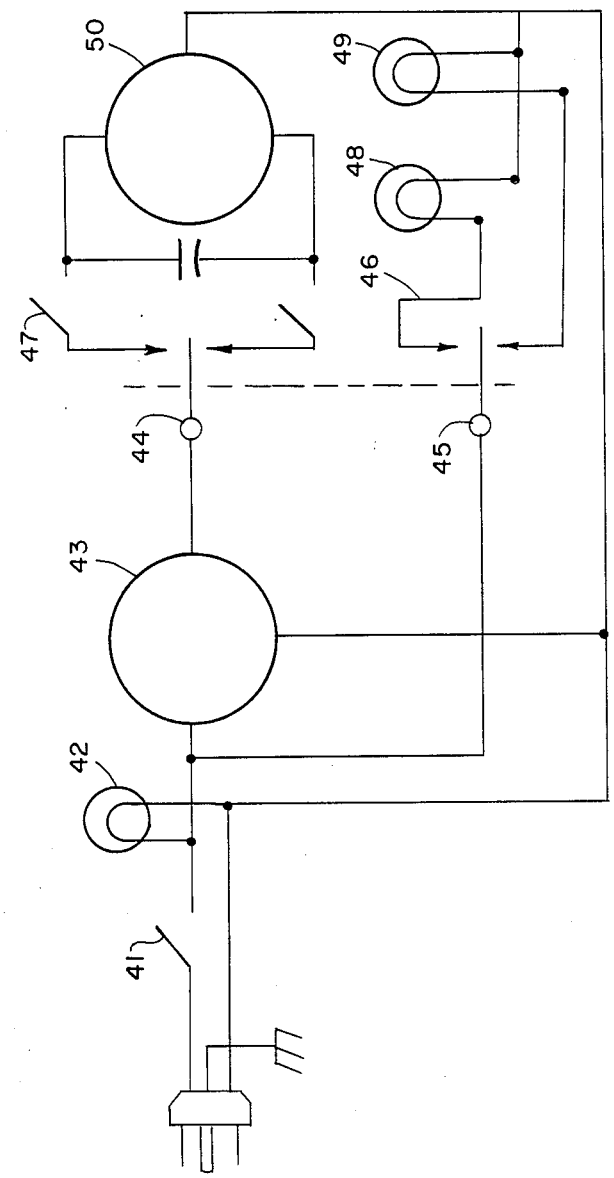
FIG. 2 is a schematic of an embodiment of the electrical components used in the apparatus.

FIG. 2 shows a schematic diagram for the electrical components used in the apparatus according to the present invention. The two SPST-NC momentary microswitches 15 attached to the back of the apparatus are optional. These switches govern the stroke length of the Plexiglass case. By adjusting the position of the switches, the operator is allowed to limit the distance the syringes will move. Once the system is set up, the limit switches will automatically terminate the stroke, thereby providing the desired gradient volume. The neon pilot light 17 for the up stroke and the neon pilot light for the down stroke 19 are separated by a directional toggle switch 18. The unit power toggle switch 21 controls the operation of the entire apparatus. The neon pilot lamp for unit power is shown at 20.

Of course, the controls described in FIG. 2 are illustrative, and can be of any type which will provide the required action. For example, the controls can be computer driven.

In FIG. 2, the gradient former is activated by the unit power toggle switch 41. The neon pilot lamp 42 provides unit power. A variable autotransformer is shown at 43. Directional toggle switches are shown at 44 and 45, and momentary microswitches for up and down strokes are shown at 46 and 47. Neon pilot lamps are shown 48 and 49. The gear motor, 50, may be a capacitor gear motor or a stepping motor.

Figure 4:
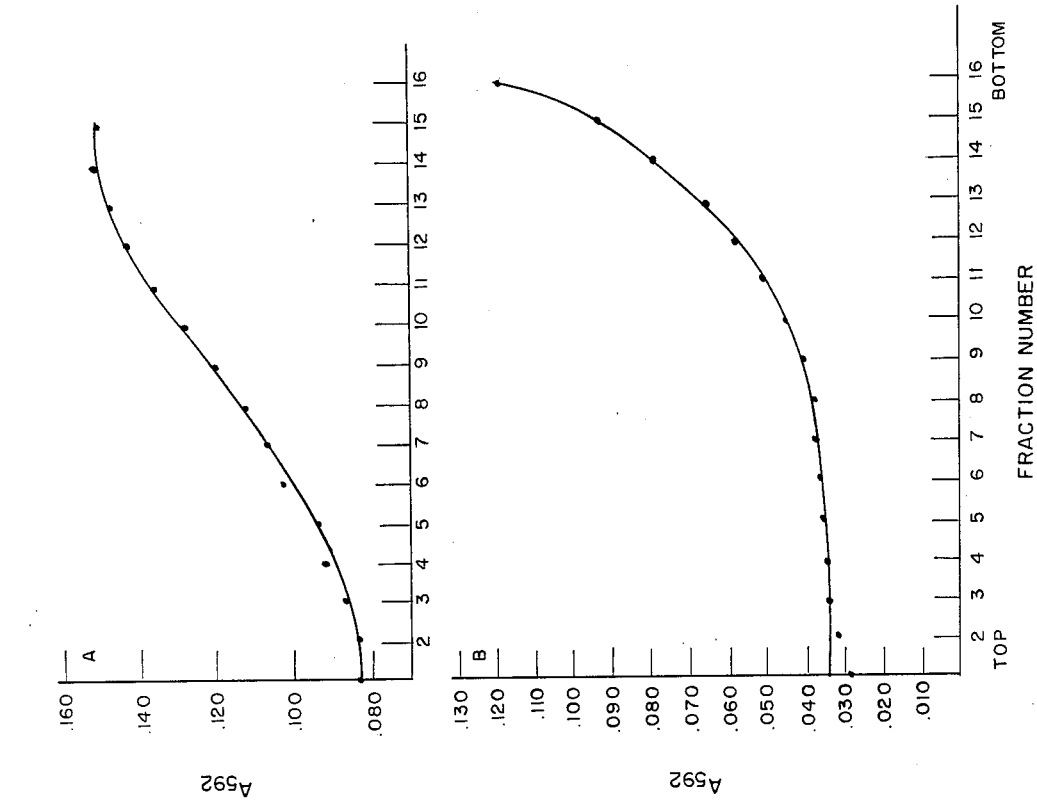
FIG. 4 shows a sucrose step gradient composed of equal volumes of 2.5, 5.5, 11, and 22 percent sucrose solution which also contains bromophenol blue.
Figure 3:
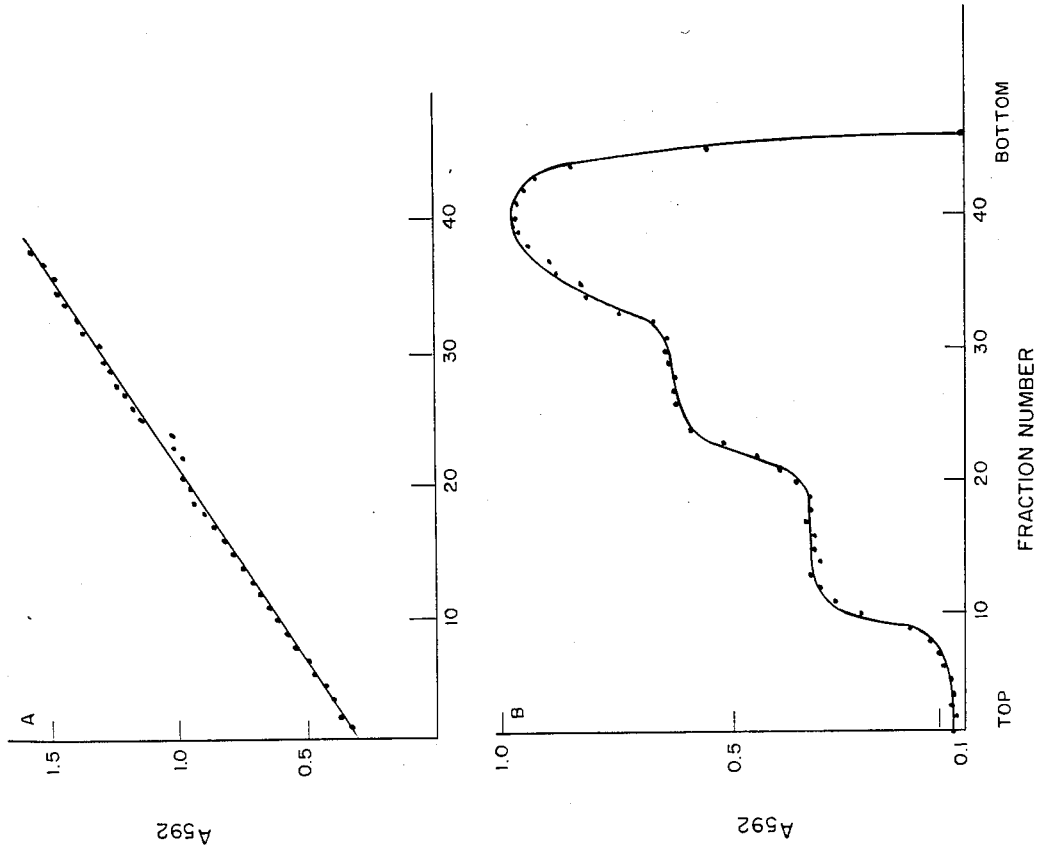
FIG. 3 shows a linear 22 to 44% sucrose gradient which was made by apparatus of the present invention.

FIGS. 3 and 4 show examples of the shapes of gradients which can be made in multiples, i.e., six at a time, by the apparatus of the present invention.

FIG. 3 shows a linear 22 to 44% sucrose gradient which was made and immediately fractionated. The dense sucrose solution contained bromophenol blue so that the shape of the gradient could be measured as a change in the optical density (at 592 A). Other gradients assayed from this set as well as from other sets gave similar plots. Points randomly fell off the line due to fractionation discrepancies.

FIG. 4 shows a sucrose step gradient composed of equal volumes of 2.5, 5.5, 11, and 22 percent sucrose solution which also contained bromophenol blue. The step gradient was formed over a 1 ml shelf of 44% sucrose which did not contain the bromophenol blue. Fractions were collected and assayed as above.

The process according to the present invention requires that all of the vacuum devices (syringe plungers, etc.) move through the same distance, so that each receptacle receives an equal volume of liquid from a mixing chamber simultaneously, and the low density devices (syringes, etc.) are forced to deliver the desired amount of light material to the mixing chamber. The displacement of the vacuum devices and the low density devices can be adjusted to provide the desired mixing ratio of dense/light solution.

Figure 1:
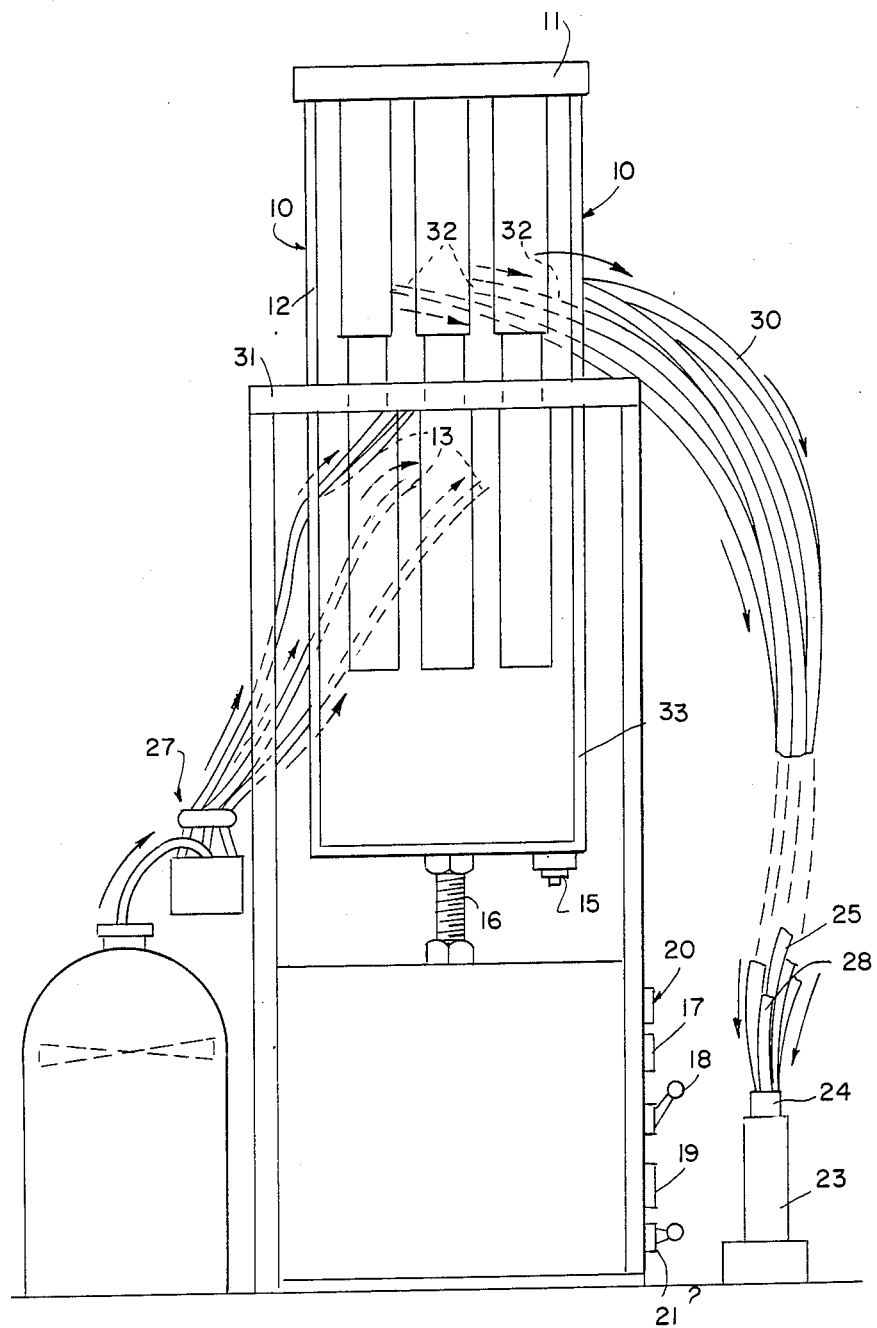
FIG. 1 shows a front view of the apparatus of the present invention.

To make six linear 10 ml continuous gradients using the apparatus as described above, each of the three low density syringes and lines are filled with a low density solution (10 ml) and set in place as shown in FIG. 1. The top block 11 is set into place by gently slipping it between the syringe plungers and the Plexiglass case 12. Dense solution (30 ml) is placed into the mixing chamber and the centrifuge-cork junctions are sealed with rubber cement. The motor is turned on and its speed is regulated to 25 rpm by using a variable speed transformer 20. Rotation of the lead screw 16 lowers the Plexiglass case 12 causing expansion of the six vacuum syringes 29 which create six identical vacuums in the centrifuge tubes 23. These vacuums must be equal because all vacuum syringe plungers move through the same distance. As a result, all centrifuge tubes receive identical volumes of liquid from the mixing chamber. Simultaneously, the three low density syringes 32 are forced to deliver the proper amount of light material to the mixing chamber 28. Because the displacement of the vacuum syringes and the low density syringes are equal, a 2:1 dense:light mixing ratio is preserved at all times. It has been found convenient to form 10 ml gradients slowly over an interval of 45 minutes, although this period can be greater or less, depending on the application. This avoids turbulent mixing of the gradient as it forms within the centrifuge tube and is a convenient interval of time for attending to other experimental procedures. However, acceptable gradients may be formed in as little as 20 minutes.

To make step gradients, the denser material is simply added to the mixing chamber. After the mixing chamber becomes empty, the next solution is added, etc.

The process can be used with any apparatus that generates a vacuum to draw fluid which can then be transferred to a suitable receptacle.

As discussed above, FIGS. 3 and 4 show some of the types of gradients which can be formed by the apparatus of the present invention. Other types of gradients, such as convex exponential gradients, can be made. In a similar manner, combination gradients may be generated. For example, a two step discontinuous gradient consisting of a 1 ml shelf of 44% sucrose and a linear gradient of 24 to 44% may be made. The variation in shapes of gradients, as well as concentration ranges, is limitless. Obviously, the use of the apparatus is not limited to making sucrose gradients, but can be used for generating any type of gradient, such as temperature or color gradients.

It has been found that the gradients within a set are identical in both shape and concentration range. It has also been found that gradients vary little in shape from set to set, provided that the same stock solutions and conditions were used to generate the gradients. Linear 22 to 44% sucrose gradients were frozen at 20° C. in nitrocellulose tubes. It was found, upon being thawed and brought to 4° C., that the gradients retained a gradient shape similar to that shown in FIG. 3. Accordingly, in an eight hour work day, 48 gradients can easily be made and frozen for use at a later time. This approach of using preformed frozen gradients can be used to reduce the work load on busy research days. This method also provides uniform gradients for experiments which require samples to be loaded and/or run over an extended period of time.

The process of the present invention is particularly advantageous in that it provides a method for forming multiple gradients that are of analytical quality.

The apparatus of the present invention as illustrated has been used to prepare sucrose gradients, in one instance for use in separating subcellular components of the cellular slime mold *Dictyostelium discoideum*. The apparatus obviously can be adapted to other uses. The apparatus can be constructed to produce a larger or smaller number of gradients as demanded by specific needs. Since the apparatus relies solely on vacuum-mechanical forces, it can be scaled to any size. The apparatus also ensures the proper rate of mixing without the use of pumps and their related problems. The process provides the first analytical multiple gradient former.

It will thus be seen that the objects set forth above, among those made apparent from the preceding description, are efficiently attained. Since certain changes may be made in the constructions set forth above without departing from the scope of the invention, it is intended that all matter contained in the above description or shown in the accompanying drawings shall be interpreted as merely illustrative and not limiting.

What is claimed is:

1. A method for forming a plurality of serial dilutions comprising:
   providing a supply of solution to be mixed;
   transferring said solution to a mixing chamber containing diluent for mixing with the desired amount of diluent;
   transferring solution from said mixing chamber through a plurality of delivery lines into a plurality of receptacles, said transferring being effected by applying metered negative pressure to each delivery line to remove the same amount of solution from said mixing chamber and by applying metered pressure to each delivery line to deliver a metered amount amount of solution to each receptacle.

2. The process of claim 1 wherein continuous gradients are produced.

3. The process of claim 1 wherein discontinuous gradients are produced.

4. The process of claim 1 wherein multiple identical serial dilutions are produced.

5. Apparatus for forming a plurality of serial dilutions comprising:
   means for drawing gradient material from a common mixing chamber;
   means for delivering gradient material through delivery lines into a plurality of receptacles;
   said means for delivering gradient material comprising means for creating metered negative pressure on each delivery line to remove gradient material from said mixing chamber, and means for creating metered pressure on each delivery line for delivering gradient material to each receptacle.

6. The apparatus of claim 5 wherein the means for drawing gradient material comprises syringes.

7. The apparatus of claim 6 wherein the vacuums are identically metered.

* * * * *